(12) United States Patent
Inaba

(10) Patent No.: US 7,680,246 B2
(45) Date of Patent: Mar. 16, 2010

(54) METHOD AND DEVICE FOR JUDGING POLARITY OF SINGLE CRYSTAL SAMPLE

(75) Inventor: Katsuhiko Inaba, Ome (JP)

(73) Assignee: Rigaku Corporation, Akishima-Shi (JP)

( * ) Notice: Subject to any disclaimer, the term of this patent is extended or adjusted under 35 U.S.C. 154(b) by 143 days.

(21) Appl. No.: 11/991,495

(22) PCT Filed: Aug. 30, 2006

(86) PCT No.: PCT/JP2006/317095

§ 371 (c)(1),
(2), (4) Date: Mar. 5, 2008

(87) PCT Pub. No.: WO2007/040000

PCT Pub. Date: Apr. 12, 2007

(65) Prior Publication Data

US 2009/0225946 A1    Sep. 10, 2009

(30) Foreign Application Priority Data

Sep. 5, 2005    (JP) .............................. 2005-257154

(51) Int. Cl.
*G01N 23/207* (2006.01)
(52) U.S. Cl. .......................................... 378/73; 378/71
(58) Field of Classification Search .................. 378/70, 378/71, 73
See application file for complete search history.

(56) References Cited

U.S. PATENT DOCUMENTS 6,807,251 B2 * 10/2004 Okanda et al. ................ 378/71

(Continued)

FOREIGN PATENT DOCUMENTS

JP    3691827 B2    6/2005

(Continued)

OTHER PUBLICATIONS

Barns, et al, "X-Ray Determination of Polarity Sense by Anomalous Scattering at an Absorption Edge," Journal of Applied Crystallography, vol. 3, 1970, pp. 27-32.

(Continued)

*Primary Examiner*—Allen C. Ho
(74) *Attorney, Agent, or Firm*—Frishauf, Holtz, Goodman & Chick, P.C.

(57) ABSTRACT

Wavelength dependence of diffraction X-ray intensity of a single crystal sample is measured using an X-ray incident optical system of simple structure so that the polarity of the single crystal sample can be judged. When the polarity of the {111} face of a GaAs single crystal sample (18) is judged, for example, an X-ray source (10) which can generate X-rays in a predetermined wavelength range including in the middle the wavelength at the K absorption end of Ga, i.e. an X-ray source of Au target, is employed. An X-ray beam (12) emitted from that X-ray source is reflected on a paraboloidal multilayer film mirror (14) to form a parallel beam (16) including an X-ray in a predetermined wavelength range. The sample (18) is irradiated with the parallel beam and the intensity of a diffraction X-ray therefrom is detected by an X-ray detector (22). Wavelength dependence of diffraction X-ray intensity is measured in the wavelength range including the wavelength at the absorption end by performing 2θ/ω scanning. Polarity is judged by determining the ratio of diffraction X-ray intensity on the shorter wavelength side than the absorption end to diffraction X-ray intensity on the longer wavelength side than the absorption on end.

12 Claims, 13 Drawing Sheets

U.S. PATENT DOCUMENTS

2004/0190681 A1 9/2004 Omote
2004/0240611 A1 12/2004 Yamaguchi et al.

FOREIGN PATENT DOCUMENTS

JP 3697246 B2 7/2005

OTHER PUBLICATIONS

Ikeda, Takeshi et al, "Epitaxial growth on MnAs on single-crystalline Mn-Zn ferrite substrates," Journal of Crystal Growth, vol. 2-8, No. 1-4, 2000, pp. 395-400.

Matsuno, Shin-Ya, et al, "X-Ray Reflectivity and Depth—Resolved In-Plane X-ray Diffraction Studied of Thin Films Using a High Performance Grazing Incidence X-Ray Scattering Apparatus," Advances in X-Ray Chemical Anaysis, Japan 30 (34th Series), 1999, pp. 189 to 203.

Minegishi, Tsutomu, et al, "Selective growth of Zn- and O-polar ZnO layers by plasma-assisted molecular beam epitaxy," Journal of Vacuum Science & Technology, B vol. 23, No. 3, May 2005, pp. 1286-1290.

Ikeda, Susumu, et al, "Epitaxial growth and domain coalescence of sexithiophene induced by the steps on cleaved Krr(001)," Journal of Crystal Growth, vol. 265, No. 1-2, 2004, pp. 296-301.

International Search Report dated Nov. 14, 2006, issued in a counterpart International Application.

Supplementary European Search Report dated Jun. 12, 2009 issued in counterpart European Appln. No. 06797068.1.

Tampo, H., et al., "Determination of crystallographic polarity of ZnO layers" Applied Physics Letters, AIP, American Institute of Physics, Melville, NY, US, vol. 87, No. 14, Sep. 26, 2005, pp. 141904-1-141904-3, XP012075858, ISSN: 0003-6951.

Dudley, M. et al., "The influence of polarity on twinning in zincblende structure crystals: new insights from a study of magnetic liquid encapsulated, Czochralski grown InP single crystals" Journal of Crystal Growth, Elsevier, Amsterdam, NL, vol. 192, No. 1-2, Aug. 15, 1998, pp. 1-10, XP004141526, ISSN: 0022-0248.

Stevenson, Andrew et al., "Structural Aspects of MOCVD-Grown Hg1-xCdxTe Layers on Novel GaAs Substrates" ACTA CRYSTALLOGRAPHICA A, vol. 47, 1991, pp. 128-133, XP002526825.

Huang, Ting "Recent developments in X-ray Diffraction Analysis" The Rigaku Journal, vol. 15, No. 1 1998, pp. 6-8, XP002526828.

* cited by examiner

[Fig. 1]
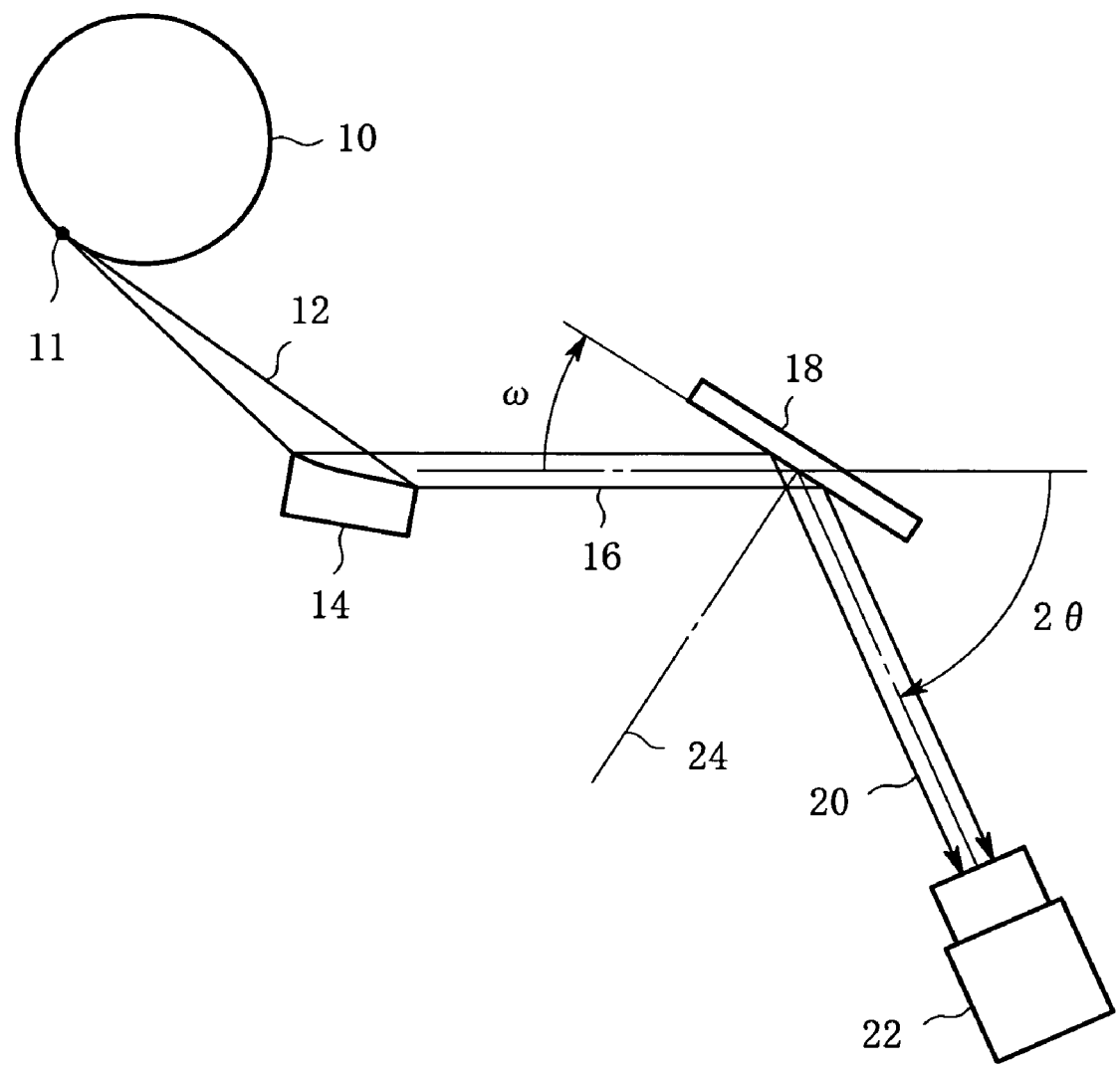

[Fig. 2]
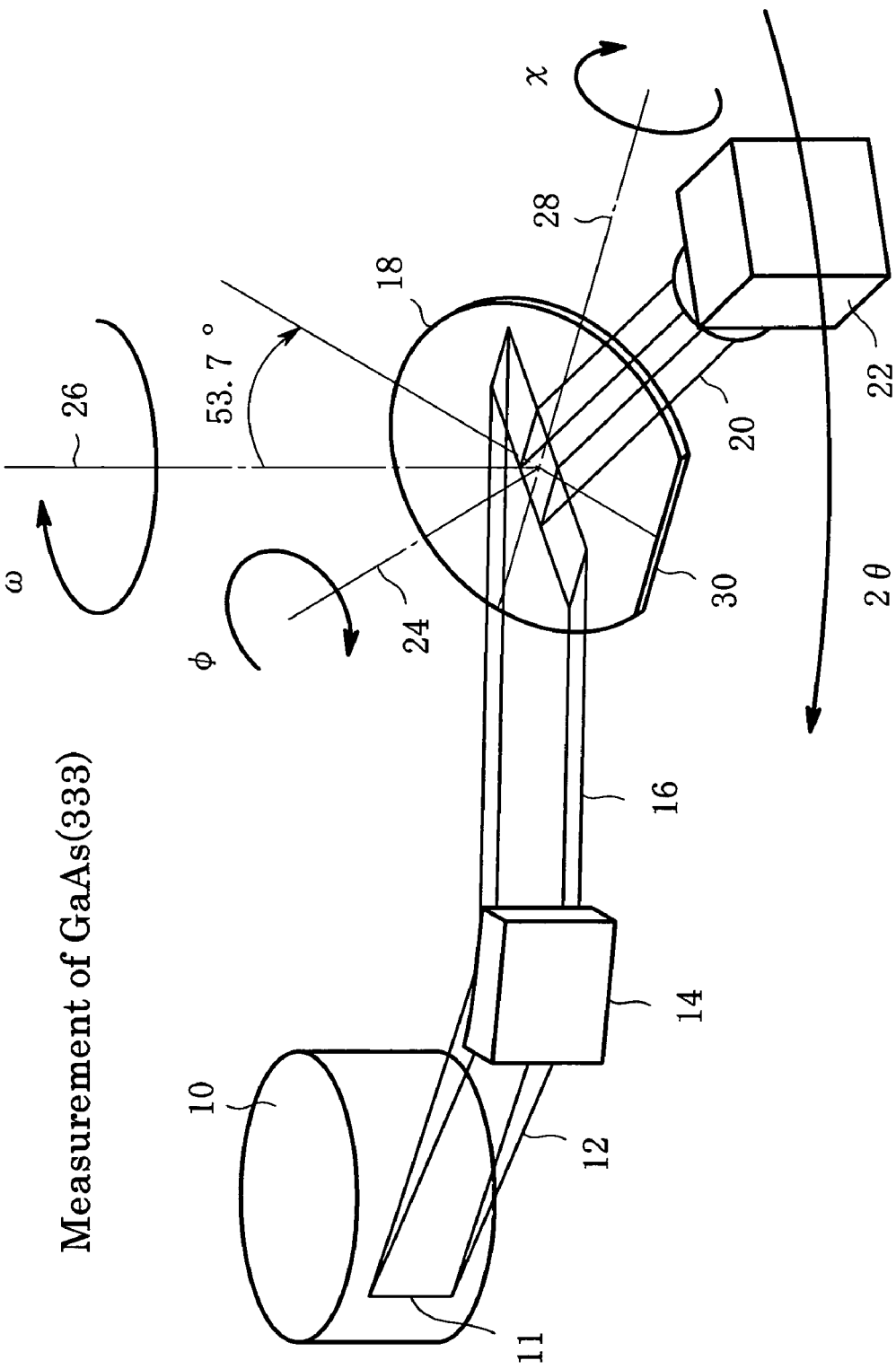

[Fig. 3]
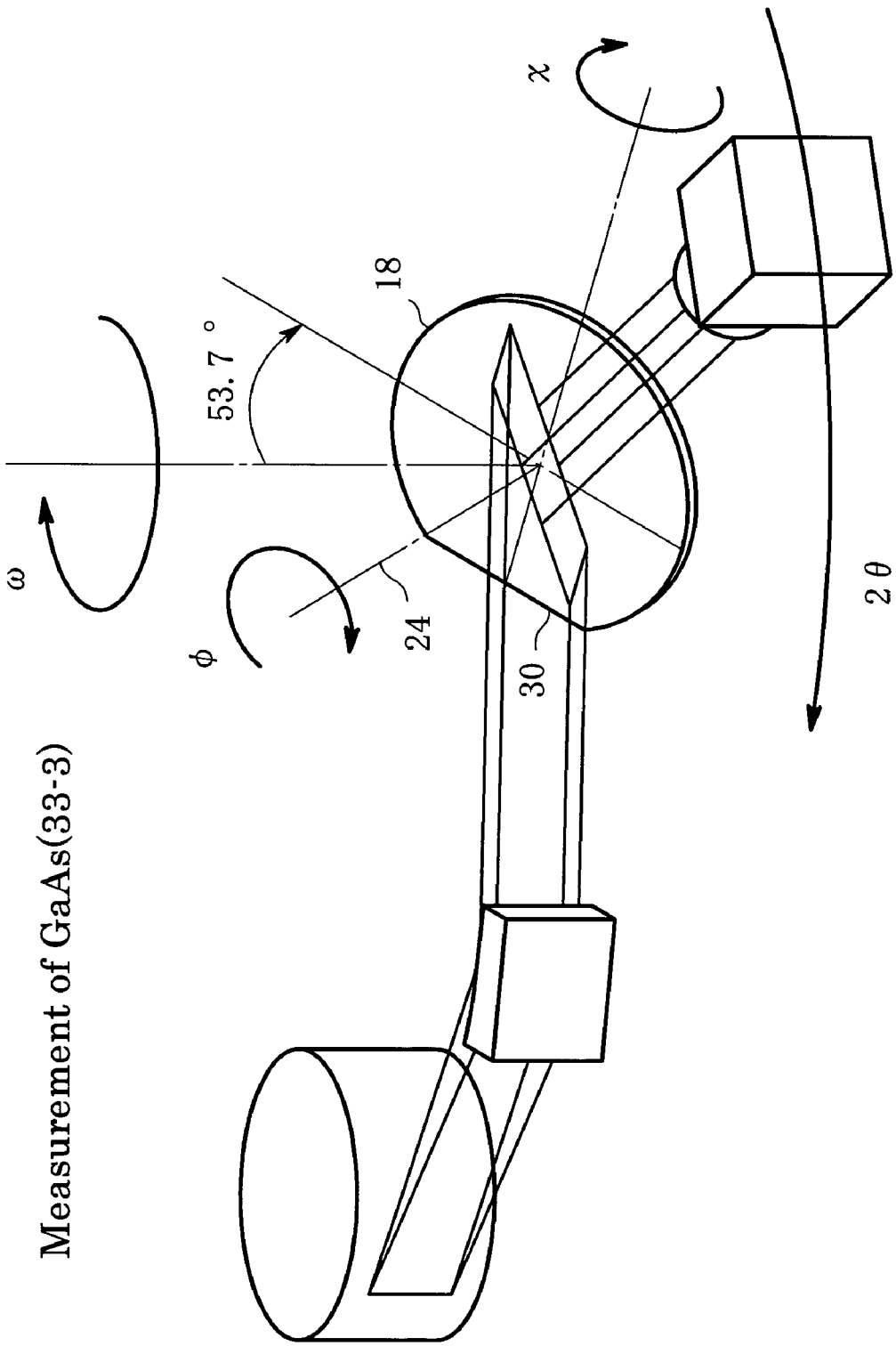

[Fig. 4]
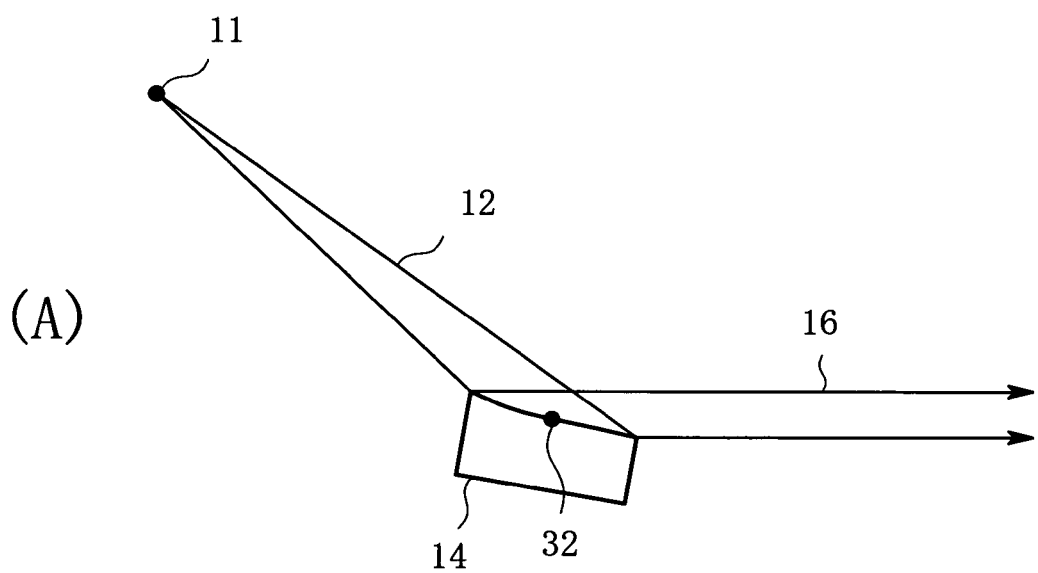
(A)
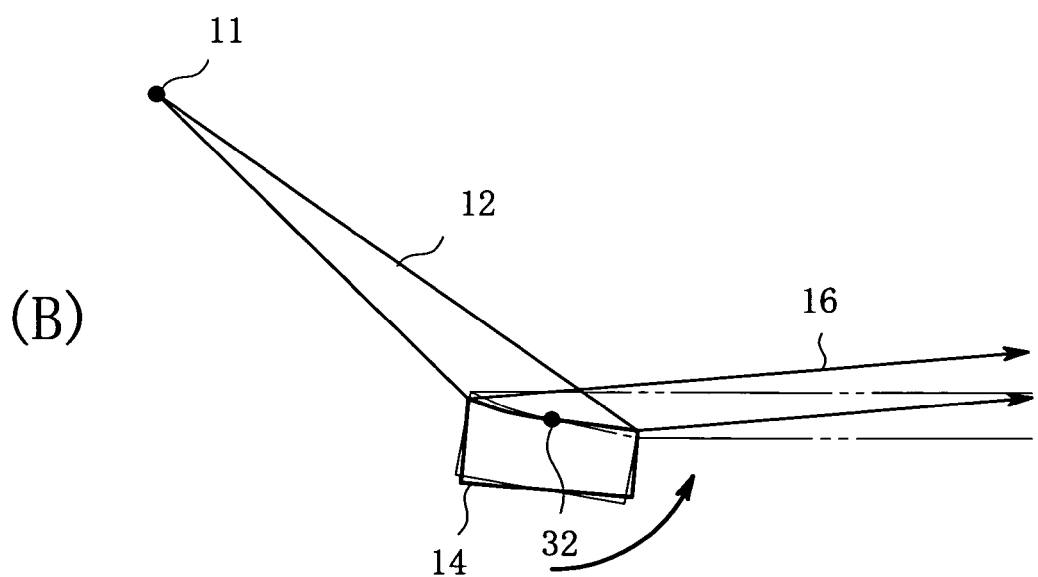
(B)

[Fig. 5]
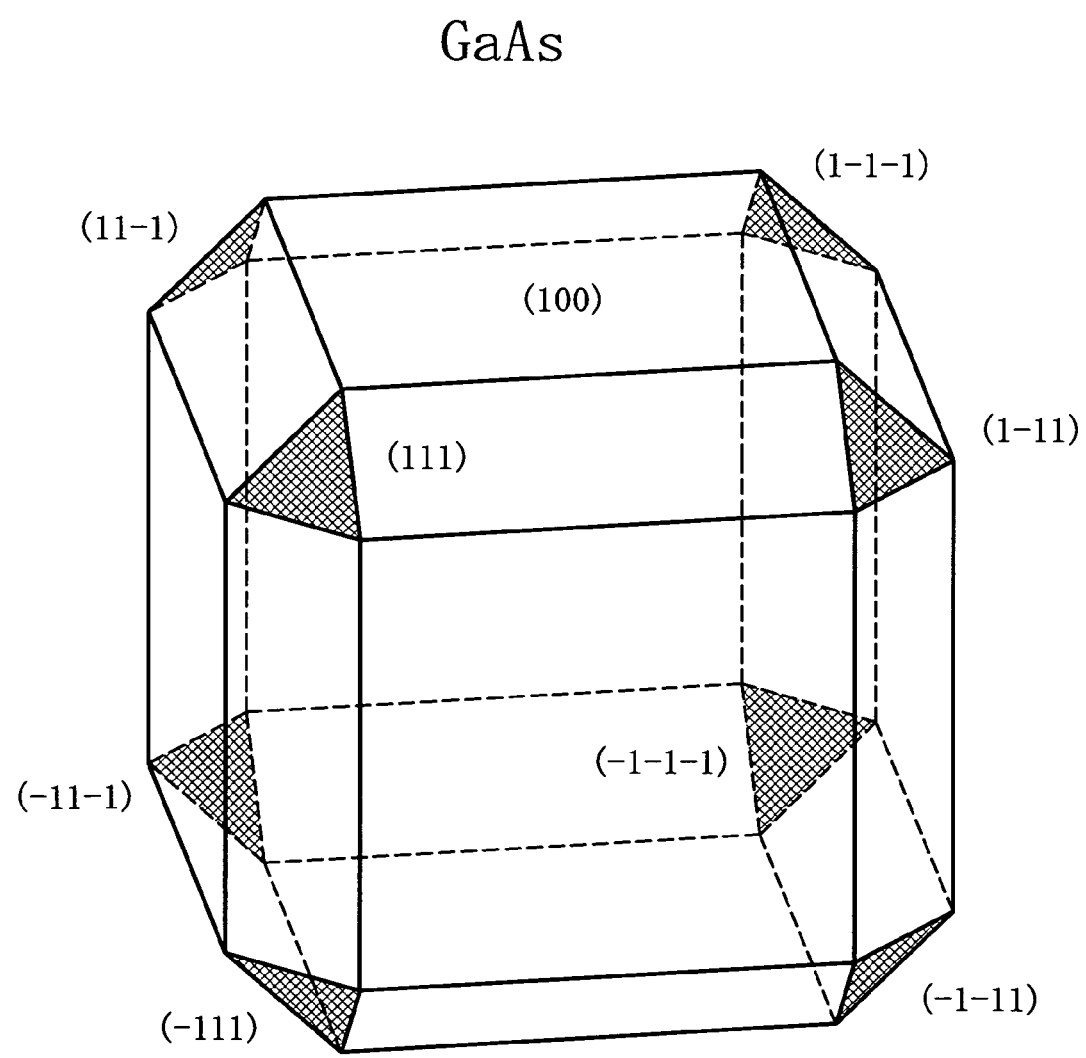

[Fig. 6]
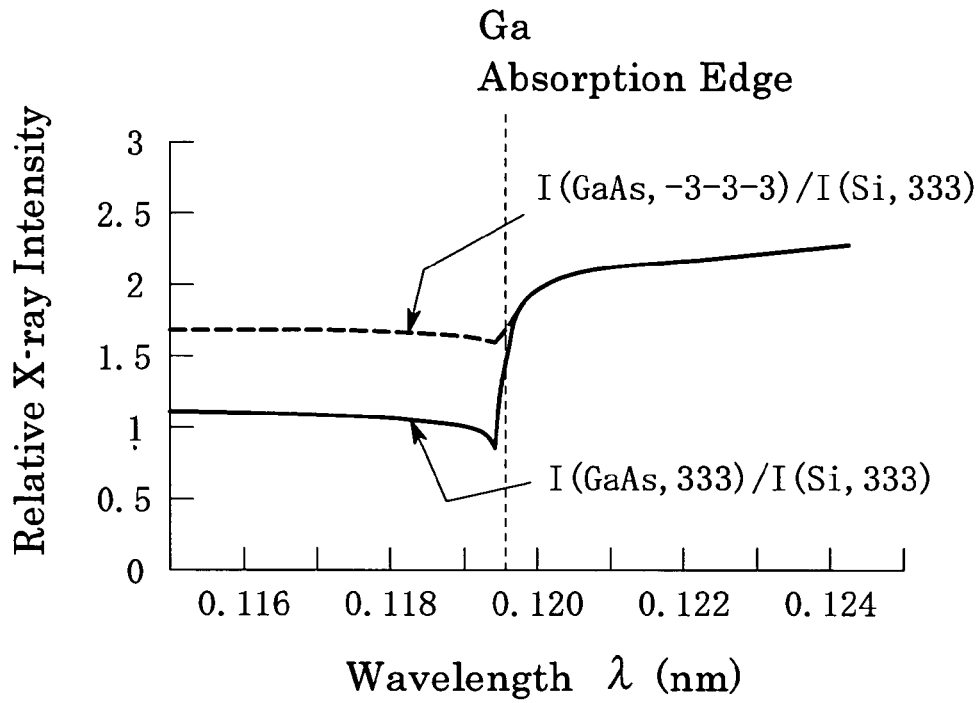
[Fig. 7]
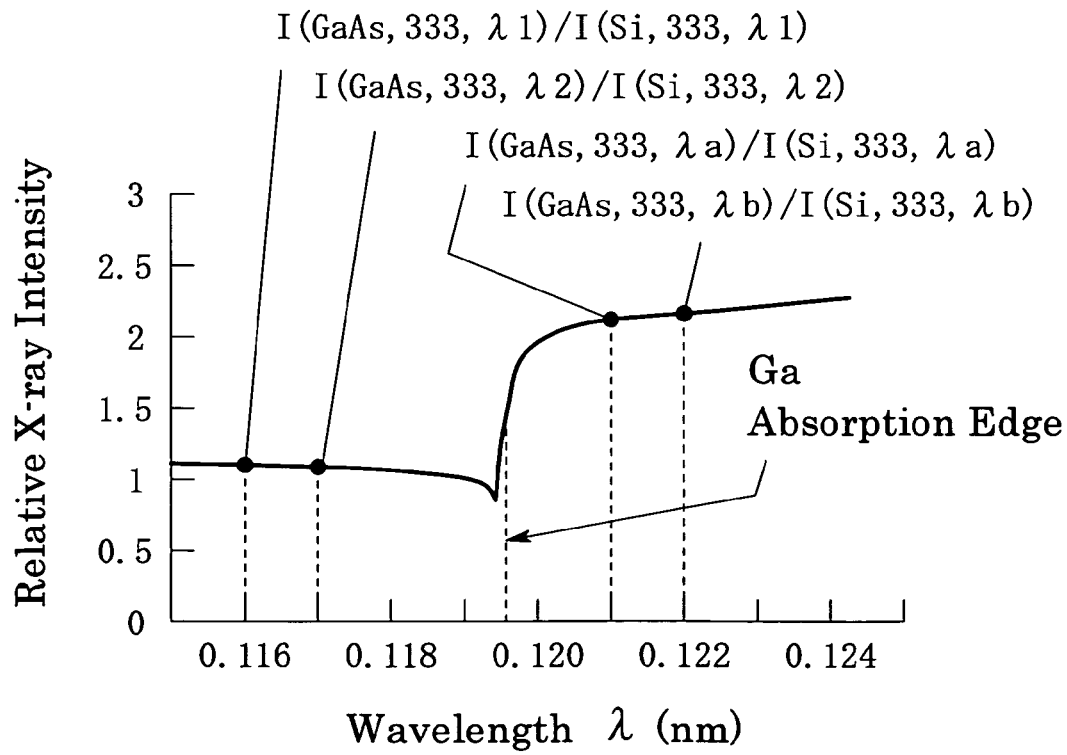

[Fig. 8]
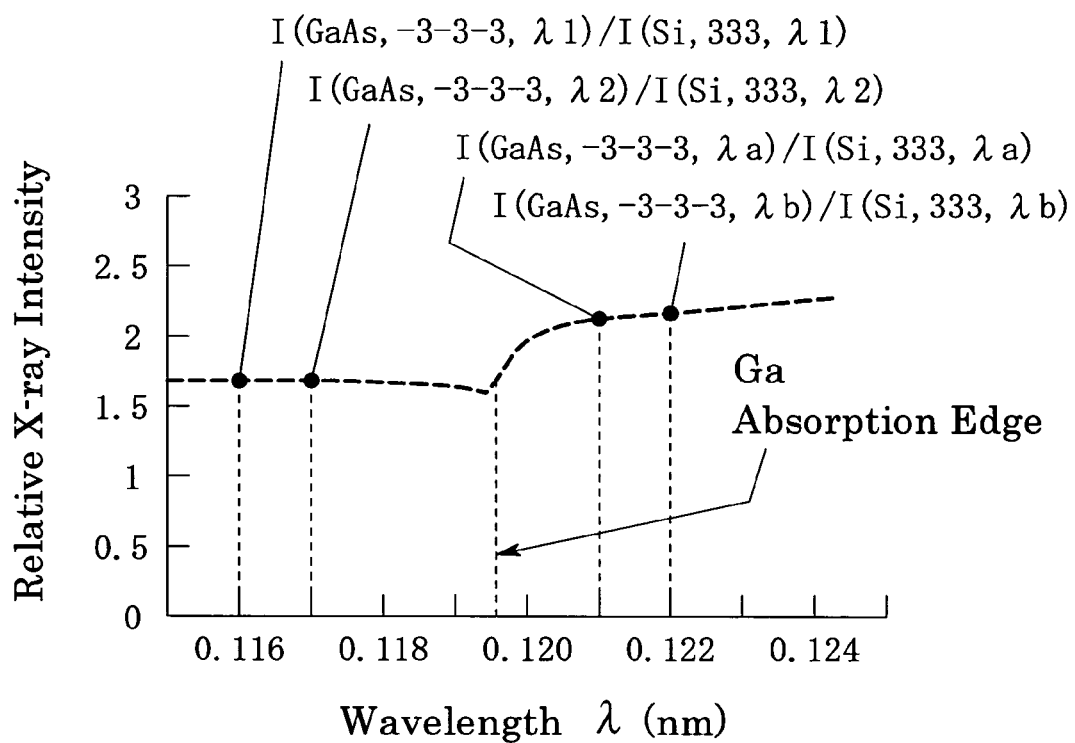

[Fig. 9]

$$\frac{I(GaAs, 333, \lambda 1)/I(Si, 333, \lambda 1) + I(GaAs, 333, \lambda 2)/I(Si, 333, \lambda 2)}{I(GaAs, 333, \lambda a)/I(Si, 333, \lambda a) + I(GaAs, 333, \lambda b)/I(Si, 333, \lambda b)} = 0.55 \quad (1)$$

$$\frac{I(GaAs, -3-3-3, \lambda 1)/I(Si, 333, \lambda 1) + I(GaAs, -3-3-3, \lambda 2)/I(Si, 333, \lambda 2)}{I(GaAs, -3-3-3, \lambda a)/I(Si, 333, \lambda a) + I(GaAs, -3-3-3, \lambda b)/I(Si, 333, \lambda b)} = 0.85 \quad (2)$$

[Fig. 10]
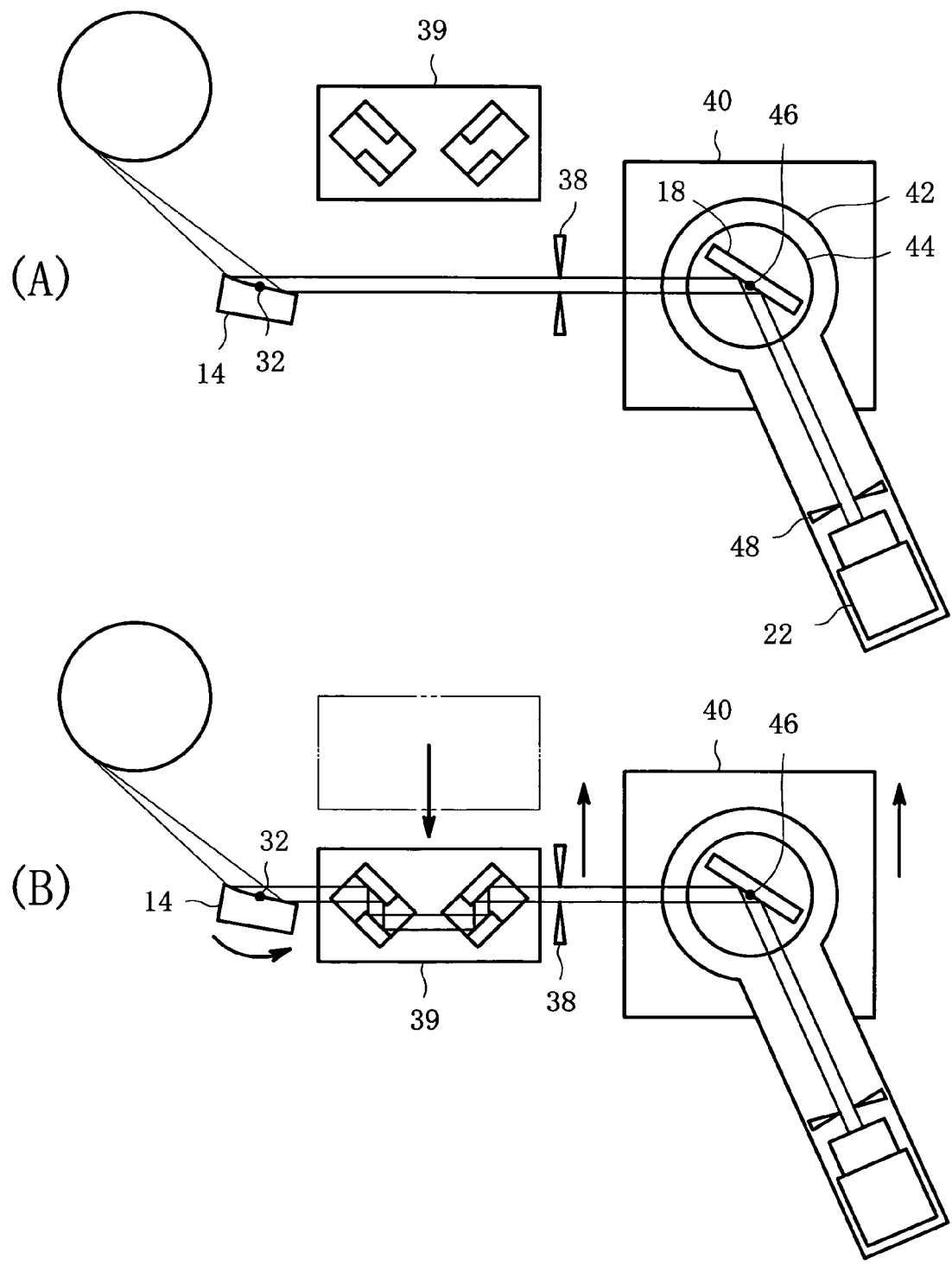

[Fig. 11]
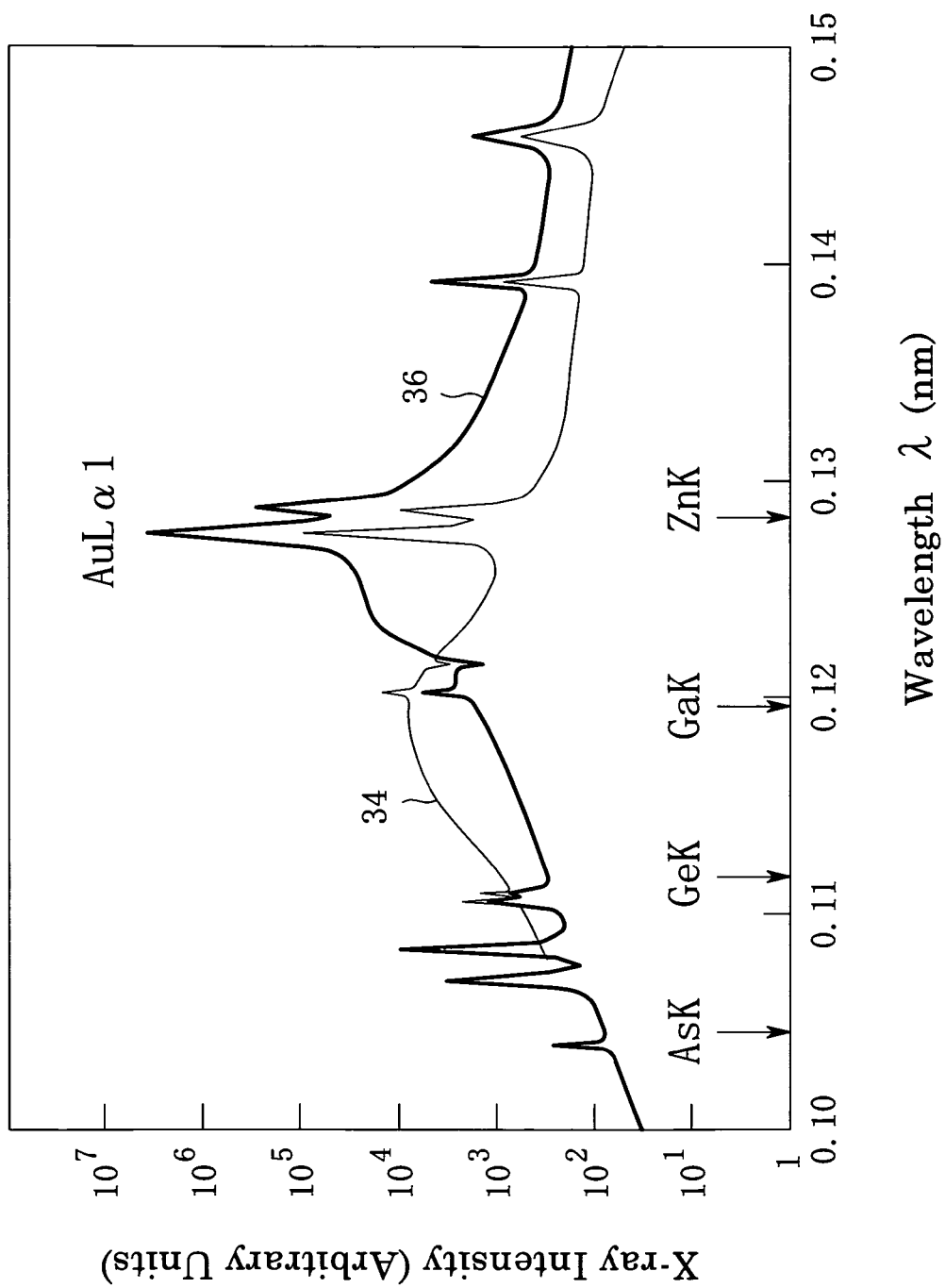

[Fig. 12]
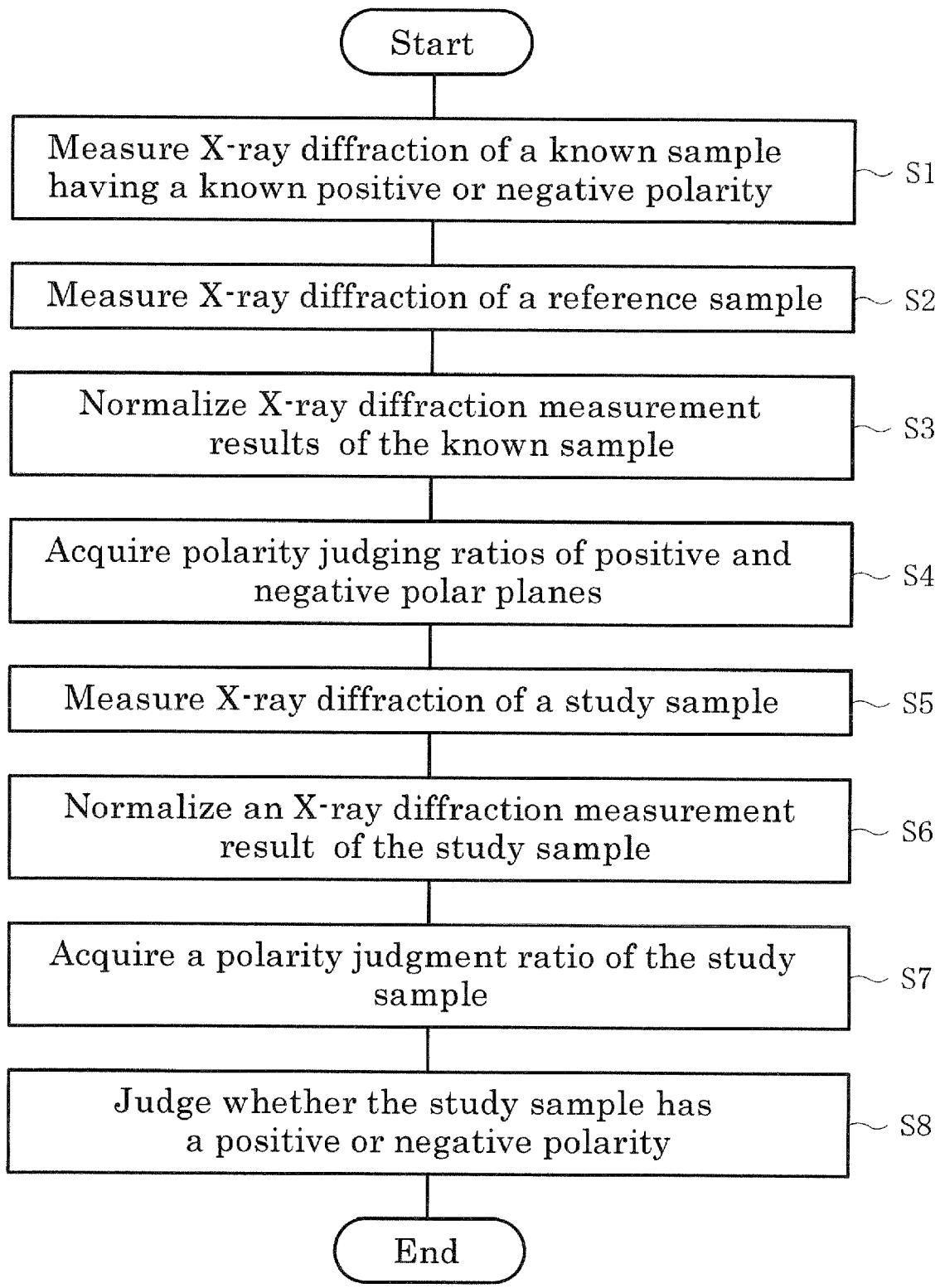

[Fig. 13]
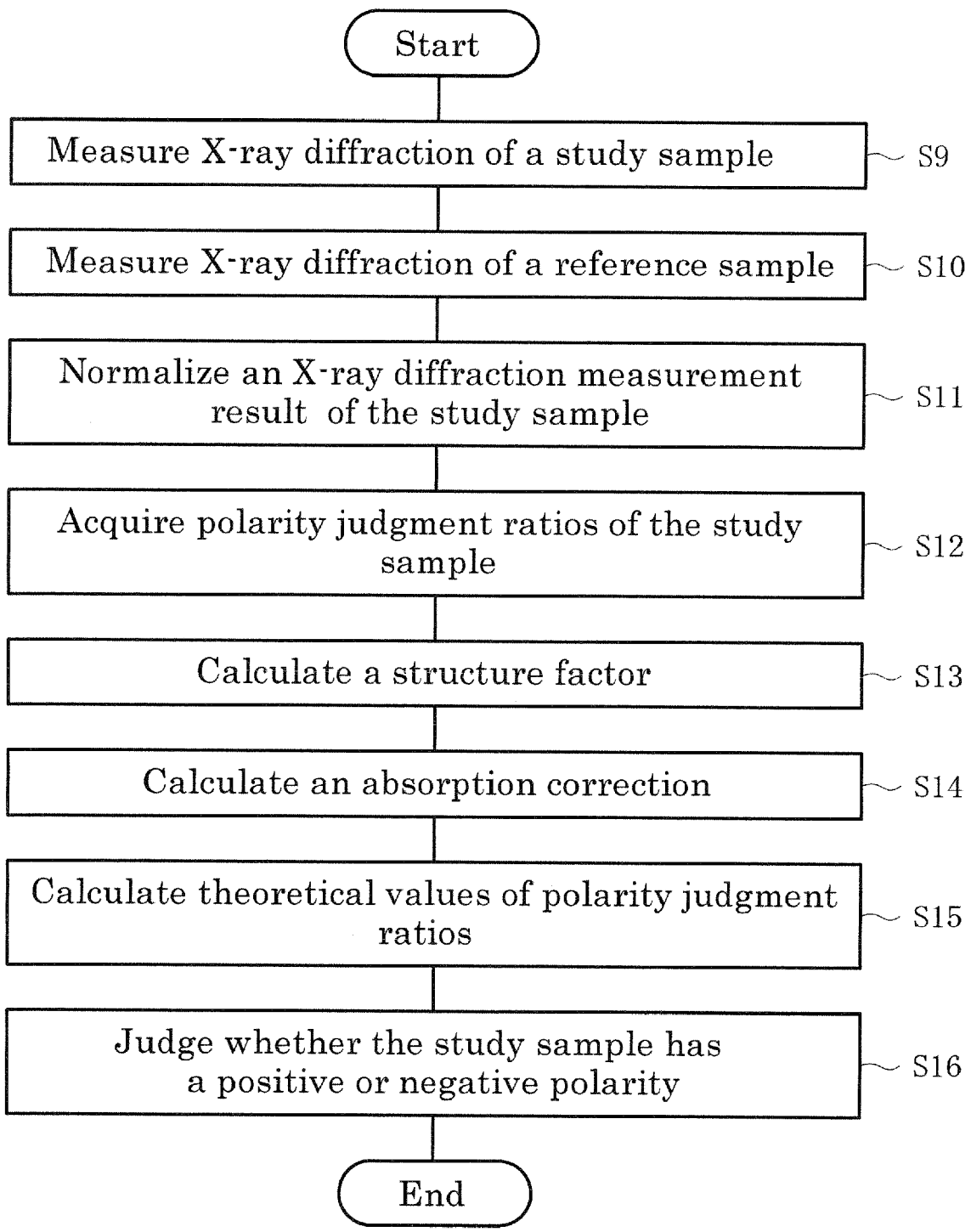

[Fig. 14]
(A) 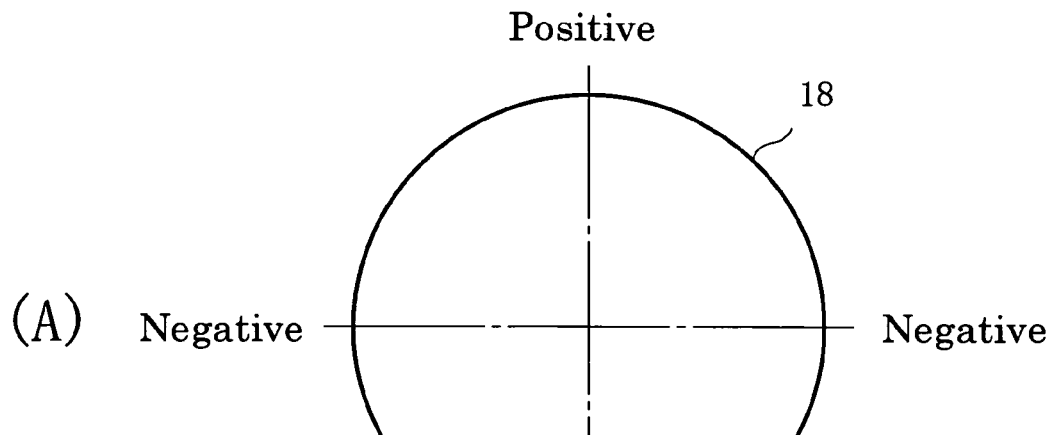
(B) 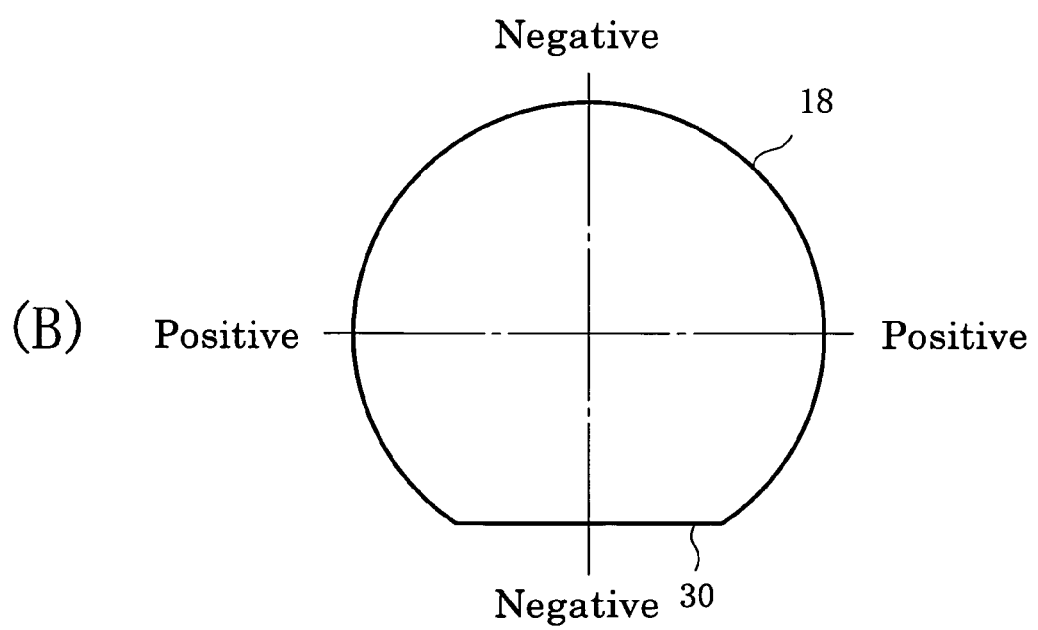

METHOD AND DEVICE FOR JUDGING POLARITY OF SINGLE CRYSTAL SAMPLE

This application is a U.S. National Phase Application under 35 USC 371 of International Application PCT/JP2006/317095 filed Aug. 30, 2008.

TECHNICAL FIELD

The present invention relates to a method and apparatus for judging the polarity of a single crystal sample with the use of an X-ray diffraction method.

BACKGROUND ART

A III-V compound semiconductor crystal such as GaAs has a polarity (i.e., a direction of crystal) in its crystal structure. FIG. 5 is a perspective view showing the major crystal lattice planes of a GaAs crystal. The GaAs crystal structure belongs to the cubic system. Assuming that the top plane in FIG. 5 is a (100) plane, eight crystal lattice planes that are equivalent of a (111) plane in the simple cubic lattice (these crystal lattice planes are marked by cross hatching in FIG. 5 and they will be expressed by Ga{111} planes) are classified to a Ga plane on which only Ga atoms exist and an As plane on which only As atoms exist. In a direction perpendicular to such a crystal lattice plane, there appear alternately the Ga planes and the As planes with different distances having a three-to-one ratio. A viewing direction from the Ga plane to the nearest As plane is opposite to a viewing direction from the As plane to the nearest Ga plane, and it is considered that physical and chemical properties depend on such a direction. Such a difference in direction of crystal is referred to as a polarity. Among the eight crystal lattice planes belonging to Ga{111}, the four equivalent crystal lattice planes (111), (1-1-1), (-11-1) and (-1-11) belonging to the Ga plane, these four crystal lattice planes being defined as a "positive polar plane". On the other hand, the four equivalent crystal lattice planes (-1-1-1), (11-1), (1-11) and (-111) belong to the As plane, these four crystal lattice planes being defined as a "negative polar plane". It is noted that the numbers in parentheses are the Miller indices and the minus sign should be attached to the trailing number after the minus sign. When the positive polar plane exists on the crystal surface, Ga atoms appear on the crystal surface. On the contrary, when the negative polar plane exists on the crystal surface, arsenic (As) atoms appear on the crystal surface.

The above-mentioned difference in polarity can not be recognized with the measurement using the ordinary X-ray diffraction method. Incidentally, a non-patent literature 1 described below discloses the polarity judgment with the use of a special X-ray diffraction method.

Non-patent literature 1: R. L. Barns and other two authors, "X-ray Determination of Polarity Sense by Anomalous Scattering at an Absorption Edge", J. Appl. Cryst. (1970) 3, 27, p. 27-32

In the non-patent literature 1, there was measured the wavelength dependence of X-ray diffraction intensity of a GaAs crystal around the K absorption edge of Ga or As. The intensity of diffracted X-rays shorter in wavelength than the absorption edge was examined, and it was found that the X-ray diffraction intensity differs between the positive and negative polar planes, and thus the polarity of the GaAs crystal can be judged on the basis of the difference. Measurement of the wavelength dependence of X-ray diffraction intensity requires a variation on of the X-ray wavelength that will be incident of the sample. For meeting the requirement, there was used, in the non-patent literature 1, a combination on of a continuous wavelength range, which is generated by an X-ray tube having a heavy metal target, and a single crystal spectrometer.

DISCLOSURE OF INVENTION

Problems to be Solved by Invention

The non-patent literature 1 mentioned above requires a large-scale X-ray incident optical system because the single crystal spectrometer is used to measure the wavelength dependence of X-ray diffraction intensity. In addition, since it is a special X-ray incident optical system, it is considered that the optical system would be hardly switched to applications other than the polarity judgment.

An object of the present invention is to provide a method and apparatus for measuring a wavelength dependence of X-ray diffraction intensity of a single crystal sample with the use of an easy structured X-ray incident optical system, and thereby judging a polarity of the single crystal sample.

Means for Solving Problems

A polarity judging method according to the present invention comprises the steps of: (a) preparing a single crystal sample, which consists of plural elements and has a polarity; (b) preparing an X-ray source, which can generate X-rays in a predetermined wavelength range including an absorption edge of any one of the plural elements; (c) allowing a divergent X-ray beam emitted from the X-ray source to be reflected by a parabolic multilayer mirror to make a parallel beam that includes the X-rays in the predetermined wavelength range; (d) allowing the parallel beam, which is used as an incident X-ray beam, to be incident on the single crystal sample, and thereafter detecting an intensity of a diffracted X-ray beam coming from the single crystal sample with an X-ray detector; (e) measuring a wavelength dependence of the intensity of diffracted X-ray beam in the wavelength range including the absorption edge of any one of the plural elements by synchronously scanning a rotation on angle $\omega$ of the single crystal sample to the incident X-ray beam and an angle $2\theta$ between the incident X-ray beam and the diffracted X-ray beam with an angular speed ratio of 1 to 2; and (f) acquiring a ratio of the intensity of diffracted X-ray beam shorter in wavelength than the absorption edge to the intensity of diffracted X-ray beam longer in wavelength than the absorption edge, and thereafter judging the polarity on a basis of a value of the ratio of intensity.

In carrying out the present invention, the intensity of diffracted X-ray beam may be normalized with the use of a reference sample having no polarity. Namely, the method may further comprises the steps of: measuring the intensity of diffracted X-ray beam for also a reference sample having no polarity as in the case with the single crystal sample having the polarity; acquiring a normalized intensity of diffracted X-ray beam by dividing the intensity of diffracted X-ray beam at each wavelength in the single crystal sample by the intensity of diffracted X-ray beam at the same wavelength in the reference sample; and acquiring the ratio of intensity on a basis of the normalized intensity.

The single crystal sample may have a wafer shape, or alternatively the sample may be a single crystal film formed on a substrate.

The single crystal sample may be a compound including any one element selected from a group consisting of Ga, Zn, Ge and As. In this case, the X-ray source has a target, whose material may be any one selected from a group consisting of Au, W and Pt. Further in this case, the multilayer mirror may be adjusted so as to reflect wavelengths around a K absorption edge of any one element selected from the group consisting of Ga, Zn, Ge and As. Alternatively, the single crystal sample may be a compound including Ta. Also in this case, the X-ray source has a target, whose material may be any one selected from a group consisting of Au, W and Pt. Further in this case, the multilayer mirror may be adjusted so as to reflect wavelengths around an L absorption edge of Ta.

In addition, a polarity judging apparatus for the single crystal sample according to the present invention comprises: (a) an X-ray tube having a target, which is made of a predetermined material; (b) a parabolic multilayer mirror, which reflects X-rays emitted from the X-ray tube to convert it to a parallel beam; (c) a sample holder for holding a single crystal sample, which consists of plural elements and has a polarity; (d) an X-ray detector for detecting a diffracted X-ray beam coming from the single crystal sample; (e) a control device for synchronously scanning a rotation on angle ω of the single crystal sample to the parallel beam and an angle 2θ between the parallel beam and the X-ray detector; (f) measurement instructing means for allowing the parallel beam, which is used as an incident X-ray beam, to be incident on the single crystal sample, and thereafter detecting an intensity of diffracted X-ray beam coming from the single crystal sample with an X-ray detector, and further measuring a wavelength dependence of the intensity of diffracted X-ray beam in a wavelength range including an absorption edge of any one of the plural elements by synchronously scanning the angle ω and the angle 2θ with an angular speed ratio of 1 to 2; and (g) judging means for acquiring a ratio of the intensity of diffracted X-ray beam shorter in wavelength than the absorption edge to the intensity of diffracted X-ray beam longer in wavelength than the absorption edge, and thereafter judging the polarity on a basis of a value of the ratio of intensity.

EFFECT OF INVENTION

With the present invention, since a parallel beam is obtained to be used as an incident X-ray beam with the use of a parabolic multilayer mirror, there is obtained an incident X-ray beam having wavelengths including a suitable range, so that the polarity judgment for the single crystal sample becomes possible with the use of a relatively simple-structured incident optical system. In addition, if the incident optical system having the parabolic multilayer mirror is re-adjusted so as to reflect the characteristic X-rays, the apparatus may be used for various X-ray analyses (for example, a high-resolution X-ray diffraction measurement using the characteristic X-rays) other than the polarity judgment. Accordingly, the X-ray diffraction apparatus for the polarity judgment may be used also as a high-resolution X-ray analysis apparatus. Furthermore, if the intensity of diffracted X-ray beam is normalized with the use of the reference sample having no polarity, there is avoided the influence of the wavelength dependence of the intensity of incident X-ray beam.

BRIEF DESCRIPTION OF DRAWINGS

FIG. 1 It is a plan view showing an example of a configuration on of an X-ray diffraction apparatus, which is used for carrying out the polarity judging method according to the present invention.

FIG. 2 It is a perspective view of a state in measuring a GaAs(333) plane with the apparatus shown in FIG. 1.

FIG. 3 It is a perspective view of a state in measuring a GaAs(33-3) plane with the apparatus shown in FIG. 1.

FIG. 4 It is a view for explaining the posture change of a multilayer mirror for changing a wavelength range that is taken out.

FIG. 5 It is a perspective view showing major crystal lattice planes of a GaAs crystal.

FIG. 6 It is a graph showing a superposition on of a measured result for a positive polar plane and a measured result for a negative polar plane.

FIG. 7 It is a graph showing a measured result for a positive polar plane only.

FIG. 8 It is a graph showing a measured result for a negative polar plane only.

FIG. 9 It shows calculation formulae for polarity judgment ratios.

FIG. 10 It is a plan view showing configuration of an X-ray analysis apparatus, which is switchable between the polarity judgment and the high-resolution X-ray analysis.

FIG. 11 It is a graph showing a comparison on between a wavelength dependence of the intensity of a parallel beam that is taken out in the state shown in the part (A) of FIG. 4 and a wavelength dependence of the intensity of a parallel beam that is taken out in the state shown in the part (B) of FIG. 4.

FIG. 12 It is a flowchart showing a polarity judgment procedure.

FIG. 13 It is a flowchart showing another polarity judgment procedure.

FIG. 14 It is a view showing examples of a sample to be examined for the polarity.

EXPLANATION OF REFERENCE NUMERALS 10 rotating target
11 X-ray focal spot
12 X-ray beam
14 multilayer mirror
16 parallel beam
18 sample
20 diffracted X-ray beam
22 X-ray detector
24 φ-axis
26 ω-axis
28 χ-axis
38 incident slit
39 four-crystal monochromator
40 goniometer base
42 2θ turntable
44 sample table
48 receiving slit

BEST MODE FOR CARRYING OUT THE INVENTION

Embodiments of the present invention will now be described in detail below with reference to the drawings. FIG. 1 is a plan view showing an example of a configuration on of an X-ray diffraction apparatus, which is used for carrying out the polarity judging method according to the present invention. A divergent X-ray beam 12 is emitted from an X-ray focal spot 11 of a rotating target 10 of a rotating anode X-ray tube, and it is converted into a parallel beam 16 (an incident X-ray beam) by a parabolic synthetic multilayer mirror 14, and thereafter it is incident on a sample 18. A diffracted X-ray beam 20 that has been diffracted by a sample 18 is detected by an X-ray detector 22. An angle of a diffracted X-ray beam 20 to the incident X-ray beam 16 is 2θ.

How to use the apparatus will be described. It is assumed that the sample is a GaAs single crystal sample having a (001) plane, which is parallel to the sample surface. It is further assumed that an X-ray wavelength to be used is the wavelength (0.11957 nanometer) of the K absorption edge of Ga. First of all, the X-ray detector 22 is set at the double angle (2θ) of the Bragg angle θ of an objective crystal lattice plane that is the objective of the polarity judgment. For example, assuming that a (333) plane of the GaAs single crystal is the objective crystal lattice plane, the Bragg angle θ is 33.3 degrees at the wavelength (0.11957 nanometer) of the K absorption edge of Ga. Next, the posture of the sample 18 is adjusted so that X-rays are reflected by the objective crystal lattice plane, which is not always parallel to the crystal surface. Incidentally, since the Bragg angle θ varies with the X-ray wavelength, an expected angle position (i.e., 2θ), at which the diffracted X-ray beam is detected, of the X-ray detector 22 should vary if the X-ray wavelength varies. In other words, if the incident X-ray beam includes X-rays in a continuous wavelength range, the wavelength dependence of the intensity of diffracted X-ray beam is to be measured in a manner that the X-ray detector 22 is moved to change 2θ, and simultaneously therewith a rotation on angle ω of the sample 18 to the incident X-ray beam 16 is synchronously scanned with half an angular speed of the X-ray detector 22 (a 2θ/ω scanning).

The parabolic synthetic multilayer mirror 14 can convert the divergent X-ray beam 12 into the parallel beam 16, which has a certain degree of broadening in wavelength. The parallelism is, for example, within 0.05 degree in X-ray divergent angle. The wavelength broadening is a degree sufficient to the polarity judgment: about twenty percent in $\Delta\lambda/\lambda$ for example. The wavelength broadening may be smaller (about one percent for example) and it would be sufficient to the polarity judgment. In addition, the single crystal sample itself is allowed to have the spectrometric function (i.e., by conducting the 2θ/ω scanning), so that the wavelength dependence of the diffraction intensity can be measured. Accordingly, the wavelength dependence of the diffraction intensity can be measured without the use of the large-scale single crystal spectrometer such as one for use in an EXAFS apparatus but with the use of the multilayer mirror 14 only.

Next, there will be described a measurement example using a GaAs wafer. FIG. 2 is a perspective view of the apparatus shown in FIG. 1 in a state in measuring the positive polar plane belonging to a {333} plane of the GaAs wafer, i.e., a (333) plane. The material of the rotating target 10 is Au (gold). The GaAs wafer 18 is attached to a sample holder, which is rotatable around three axes. Explaining the three-axis rotation on, there exists at first an ω-axis 26, which coincides with the axis of rotation on (which extends vertically) of the goniometer, the wafer 18 (sample) being ω-rotatable around the ω-axis 26. Next, the wafer 18 is χ-rotatable around the χ-axis 28, which extends horizontally along the surface of the wafer 18. Further, the wafer 18 is φ-rotatable around the φ-axis 24, which is perpendicular to the surface of the wafer 18. The wafer 18 is assumed to have the upright posture that brings the orientation flat 30 lowermost, and the (001) plane of GaAs is assumed to be parallel to the wafer surface. Under the condition, the χ-axis 28 (i.e., the wafer 18) is rotated around the ω-axis 26 from the state parallel to the incident X-ray beam 16 by 33.3 degrees in the clockwise direction as viewed from the top, and further the wafer 18 is rotated around the χ-axis 28 by 53.7 degrees in the clockwise direction as viewed from the right in FIG. 2. Under the resultant posture, X-rays having the wavelength (0.11957 nanometer) of the K absorption edge of Ga are diffracted by the GaAs(333) plane, and thereafter the diffracted X-ray beam 20 is detected by the X-ray detector 22. If an X-ray diffraction profile is measured by conducting the 2θ/ω scanning around 33.3 degrees in ω, there can be measured the wavelength dependence of the intensity of diffracted X-ray beam that comes from the GaAs(333) plane. In this case, the above-mentioned 2θ/ω scanning is automatically carried out under the command of the control device. In addition, the wavelength dependence of the intensity of diffracted X-ray beam is automatically measured in the predetermined wavelength range including the wavelength of the K absorption edge of Ga under the control of the measurement instructing means, which is attached to the control device.

Next, there will be described a measurement of the negative polar plane. When the wafer 18 is rotated from the state shown in FIG. 2 by 90 degrees around the φ-axis 24 in the clockwise direction, the posture of the wafer 18 becomes the state shown in FIG. 3. Namely, the orientation flat 30 comes to the left side of the wafer 18. If the X-ray diffraction measurement is carried out under the condition as is the case shown in FIG. 2, there can be measured the wavelength dependence of the intensity of diffracted X-ray beam that comes from the GaAs(33-3) plane.

FIG. 6 is a graph showing a superposition of a measured result for the positive polar plane and a measured result for the negative polar plane. The intensity of diffracted X-ray beam of the positive polar plane is expressed by I(GaAS, 333), and this I(GaAS, 333) is divided by the intensity of diffracted X-ray beam I(Si, 333) of the (333) plane of Si (silicon), which is the reference sample, at the same wavelength to normalize the diffraction intensity. The normalization eliminates the influence of the wavelength dependence of the intensity of incident X-ray beam. Accordingly, such a relative X-ray intensity is on ordinate, whereas the X-ray wavelength is on abscissa. The graph of FIG. 6 indicates the data in the wavelength ranging from 0.115 nanometer to 0.125 nanometer. The wavelength range corresponds to a continuous wavelength part of the wavelength band near the Au-Lη characteristic X-rays.

When the X-ray diffraction measurement is carried out in the states shown in FIGS. 2 and 3, there is obtained a variation on of the intensity of diffracted X-ray beam in response to a variation on of 2θ, noting that if 2θ is converted into the wavelength λ, the graph of FIG. 6 is obtained. The conversion of 2θ to the wavelength λ is made by calculation with the Bragg's formula with the use of the lattice spacing value of Ga(333). The intensity of diffracted X-ray beam I(GaAs, −3-3-3) of the negative polar plane is similarly measured. It is noted that although the actual measurement was conducted for Ga(33-3) in FIG. 3, the measurement result is expressed as the data of Ga(−3-3-3). The planes of Ga(33-3) and Ga(−3-3-3) both belonging to the negative polar plane and thus they are equivalent crystal lattice planes.

It is seen in FIG. 6 that the intensity of diffracted X-ray beam is almost the same between the positive and negative polar planes in the range longer in wavelength (i.e., in the range smaller in energy) than the K absorption edge of Ga. In contrast, the intensity of diffracted X-ray beam widely differs between the positive and negative polar planes in the range shorter in wavelength (i.e., in the range greater in energy) than the K absorption edge of Ga. With the use of the difference, the judgment becomes possible between the positive and negative polar planes.

FIG. 7 is a graph showing a measured result for the positive polar plane only. Finding the relative X-ray intensity at λ1 (=0.116 nanometer) and λ2 (=0.117 nanometer) both shorter in wavelength than the K absorption on edge (λ=0.11957 nanometer) of Ga, these become I(GaAs, 333, λ1)/I(Si, 333, λ1) and I(GaAs, 333, λ2)/I(Si, 333, λ2) respectively, their values each being about 1.1. Similarly, finding the relative X-ray intensity at λa (=0.121 nanometer) and λb (=0.122 nanometer) both longer in wavelength than the K absorption edge of Ga, these are expressed by I(GaAs, 333, λa)/I(Si, 333, λa) and I(GaAs, 333, λb)/I(Si, 333, λb) respectively, their values each being about 2.0.

On the basis of these values, there is obtained, for the positive polar plane, a ratio of the intensity of diffracted X-ray beam shorter in wavelength than the absorption edge to the intensity of diffracted X-ray beam longer in wavelength than the absorption edge (the ratio being referred to as a polarity judgment ratio), the obtained value being about 0.55 as shown in formula (1) in FIG. 9.

FIG. 8 is a graph showing a measured result for the negative polar plane only. Finding the relative X-ray intensity at λ1 (=0.116 nanometer) and λ2 (=0.117 nanometer) both shorter in wavelength than the K absorption on edge (λ=0.11957 nanometer) of Ga, these are expressed by I(GaAs, -3-3-3, λ1)/I(Si, 333, λ1) and I(GaAs, -3-3-3, λ2)/I(Si, 333, λ2) respectively, their values each being about 1.7. Similarly, finding the relative X-ray intensity at λa (=0.121 nanometer) and λb (=0.122 nanometer) both longer in wavelength than the K absorption on edge of Ga, these are expressed by I(GaAs, -3-3-3, λa)/I(Si, 333, λa) and I(GaAs, -3-3-3, λb)/I(Si, 333, λb) respectively, their values each being about 2.0.

On the basis of these values, there is obtained, for the negative polar plane, the polarity judgment ratio, which is about 0.85 as shown in formula (2) in FIG. 9.

As has been described above, there was obtained the clear difference between the polarity judgment ratios for the positive and negative polar planes: about 0.55 and about 0.85. Therefore, a measurement of the polarity judgment ratio for the Ga{111} plane whose polarity is unknown enables to judge whether it is the positive polar plane or negative polar plane. Namely, if the polarity judgment ratio becomes around 0.55 it is the positive polar plane, whereas if the polarity judgment ratio becomes around 0.85 it is the negative polar plane.

FIG. 12 is a flowchart showing a polarity judgment procedure. In step S1, there is prepared a known sample (GaAs single crystal for example), in which locations of the positive and negative polar planes are known, and then the wavelength dependence of the intensity of diffracted X-ray beam is measured, for both the positive and negative polar planes of an objective crystal lattice plane (GaAs{333} plane for example) to be examined for the polarity, by conducting the 2θ/ω scanning as shown in FIG. 1 around the wavelength of the absorption edge (K absorption edge for example) of one element (Ga for example) included in the sample. In step S2, the wavelength dependence of the intensity of diffracted X-ray beam is measured, for the predetermined crystal lattice plane (the {333} plane for example) of the reference sample (Si single crystal for example), by conducting the similar 2θ/ω scanning. In step S3, the intensities of diffracted X-ray beam, obtained in step S1, of the positive and negative polar planes of the known sample are divided by the intensity of diffracted X-ray beam, obtained in step S2, of the reference sample at the same wavelength to normalize the intensities of diffracted X-ray beam. In step S4, there is calculated, with the use of the normalized intensities of diffracted X-ray beam, a ratio of the intensity at the wavelength shorter than the absorption edge to the intensity at the longer wavelength, and then the resultant ratio is defined as the polarity judgment ratio, which is obtained for both the positive and negative polar planes. In step S5, the X-ray diffraction measurement is carried out as is the case of step S1 for a study sample (i.e., the GaAs single crystal in which locations of the positive and negative polar planes are unknown). In step S6, the intensity of diffracted X-ray beam is normalized as is the case of step S3. In step S7, the polarity judgment ratio is calculated with the use of the normalized intensity of diffracted X-ray beam of the study sample. In step S8, the polarity judgment ratio obtained in step S7 is compared to the polarity judgment ratios obtained in step S4 for the positive and negative polar planes to judge whether the polarity of the measured part of the study sample is positive or negative. The acquiring operation on for the polarity judgment ratio in steps S4 and S7 and the judgment operation on in step S8 are automatically carried out by the judgment means, which is attached to the control device.

FIG. 13 is a flowchart showing another polarity judgment procedure. In the procedure of FIG. 12, the polarity judgment ratios for the positive and negative polarities are in advance actually measured with the use of the known sample in which locations of the positive and negative polar planes are known. Alternatively, theoretical values may be used instead of the measured values. In the procedure of FIG. 13, steps S9, S10, S11 and S12 are the same as steps S5, S2, S6 and S7 in the procedure of FIG. 12. Then, in step S13 of FIG. 13, a structure factor is calculated. In step S14, an absorption correction is calculated. The structure factor and the absorption correction are necessary items for theoretically calculating the intensity of X-ray beam that has been reflected by the objective crystal lattice plane of the study sample. In step S15, there are calculated theoretical values of the polarity judgment ratios. Namely, it is assumed at first that the objective crystal lattice plane to be examined for the polarity is the positive polar plane. Then, a theoretical intensity of diffracted X-ray beam is calculated at any one wavelength longer than the predetermined absorption edge, and another theoretical intensity of diffracted X-ray beam is calculated at any one wavelength shorter than the predetermined absorption edge, and thereafter the ratio of the intensities are calculated. There is now obtained the theoretical polarity judgment ratio for the positive polar plane. Next, another theoretical polarity judgment ratio is similarly calculated with assuming that the objective crystal lattice plane to be examined is the negative polar plane. Next, in step S16, the polarity judgment ratio obtained in step S12 is compared to the theoretical polarity judgment ratios obtained in step S15 for the positive and negative polar planes to judge whether the polarity of the measured part of the study sample is positive or negative. It is noted that the reliability of the theoretically-obtained polarity judgment ratio is important in the procedure of FIG. 13, and thus it is necessary, for at least one sample having the polarity, to confirm that the theoretical polarity judgment ratio is close to the measured polarity judgment ratio well enough to be usable for the polarity judgment.

FIG. 14 is a view showing examples of a sample to be examined for the polarity. The part (A) of FIG. 14 shows a GaAs single crystal wafer 18 (sample), whose surface is parallel to the (001) plane. There exists, in the direction of the orientation flat 30, the (111) plane or (-1-1-1) plane shown in FIG. 5, i.e., the positive polar plane. In the direction rotated clockwise from the above-mentioned direction by 90 degrees around the normal of the wafer surface, the negative polar plane exists. Further, in the direction rotated by 180 degrees exists the positive polar plane, and in the direction rotated by 270 degrees exists the negative polar plane. Incidentally, if there are prepared wafers having the {111} plane in the direction of the orientation flat 30, they would include one type shown in the part (A) of FIG. 14 and the other type shown in the part (B) of FIG. 14. In the wafer 18 shown in the part (B) of FIG. 14, there exists, in the direction of the orientation flat 30, the (11-1) plane or (1-11) plane shown in FIG. 5, i.e., the negative polar plane. Further, in the directions rotated clockwise by each 90 degrees around the normal of the wafer surface, there exist the positive, negative and positive polar planes in order. In the polarity judgment method according to the present invention, if the wavelength dependence of the diffracted X-ray beam is measured at the wafer posture shown in FIG. 2 to judge the polarity, there can be determined whether the GaAs wafer is of the type shown in the part (A) of FIG. 14 or the other type shown in the part (B) of FIG. 14.

Although the samples shown in FIG. 14 are to be examined for the polarity of the single crystal wafer itself, a single crystal film (an epitaxial film for example) formed on a substrate may be the objective of the polarity judgment. It is noted, however, that when a thin film on a substrate is selected as the objective of the polarity judgment, it is preferable to subtract the diffraction data of the substrate from the measured diffraction data to make the polarity judgment, because the diffraction data of the substrate may overlap the diffraction data of the thin film.

Next, there will be described a changeover operation between the polarity judgment with the use of X-rays in a continuous wavelength range and the high-resolution X-ray analysis with the use of the characteristic X-rays. In the apparatus configuration on shown in FIG. 1, when the posture of the multilayer mirror 14 to the incident X-ray beam 12 is slightly shifted, the parallel beam 16 is changed between the state allowing it to be taken out as X-rays in a continuous range and the other state allowing it to be taken out as the characteristic X-rays. It is important, for enabling such a changeover, to use, for the polarity judgment, the continuous wavelength range existing very near to the characteristic X-rays. In the embodiment described above, the Au target is used to make the polarity judgment about the positive or negative polar plane as to the GaAs{333} plane, because the wavelength of the characteristic X-rays of the Au target is close to the wavelength of the K absorption edge of Ga.

FIG. 4 is a view for explaining the posture change of a multilayer mirror for changing a wavelength range that is taken out. In the part (A) of FIG. 14, the posture of the multilayer mirror 14 is adjusted so as to allow the incident X-ray beam 12 emitted from the X-ray focal spot 11 to be reflected by the multilayer mirror 14, so that there is taken out the parallel beam 16 having X-rays in a continuous wavelength range slightly shorter than the K absorption edge of Ga. The posture of the multilayer mirror 14 can be adjusted by its rotation on around an axis of rotation on 32, which is located at the center of the reflective surface.

Although the part (A) of FIG. 4 shows the state allowing the parallel beam 16 for the polarity judgment to be taken out, this state may be changed to the other state allowing the parallel beam 16 of the characteristic X-rays to be taken out as shown in the part (B) of FIG. 4. For example, considering the changeover from the state, shown in the part (A) of FIG. 14, allowing X-rays around the K absorption edge of Ga to be taken out to the other state, shown in the part (B) of FIG. 14, allowing the wavelength of the AuLα1 characteristic X-rays to be taken out, the changeover is successfully accomplished by a counterclockwise rotation on of the multilayer mirror 14 by 0.057 degree around the axis of rotation on 32. As just described, a required rotation on angle is very small.

FIG. 11 is a graph showing a comparison between a wavelength dependence of the intensity of a parallel beam that is taken out in the state shown in the part (A) of FIG. 4 and a wavelength dependence of the intensity of a parallel beam that is taken out in the state shown in the part (B) of FIG. 4. A curve 34 that is depicted with a thin line indicates the X-ray intensity at the state shown in the part (A) of FIG. 4, whereas a curve 36 that is depicted with a heavy line indicates the X-ray intensity at the state shown in the part (B) of FIG. 4. These curves were obtained by measurements using, as an analyzing crystal, the (004) plane of a Si single crystal, which has no absorption edge around this wavelength range. The wavelength (which is denoted by GaK in FIG. 11) of the K absorption edge of Ga is 0.11957 nanometer, whereas the wavelength of AuLα1 (one of the characteristic X-rays of Au) is 0.12763 nanometer, these being very close to each other. Therefore, a small change in angle of the multilayer mirror brings the changeover between the state allowing X-rays around the K absorption of Ga to be taken out and the other state allowing AuLα1 to be taken out.

The part (A) of FIG. 10 is a plan view showing a configuration on of an X-ray analysis apparatus, which is switchable between the polarity judgment and the high-resolution X-ray analysis, the configuration on shown in FIG. 1 being more embodied in FIG. 10. An incident slit 38 is arranged between the multilayer mirror 14 and the sample 18. A four-crystal monochromator 39 can be inserted into and removed from a space between the multilayer mirror 14 and the incident slit 38. The multilayer mirror 14 is rotatable around the axis of rotation on 32. The incident slit 38 is moveable up and down in FIG. 10. A goniometer base 40 is provided with a rotatable 2θ turntable 42 and a rotatable sample table 44, both of which can rotate independently around the axis of rotation on 46 of the goniometer. The 2θ turntable 42 is provided with a receiving slit 48 and the X-ray detector 22. The goniometer base 40 is moveable up and down in FIG. 10.

The part (A) of FIG. 10 shows the apparatus state for making the polarity judgment of a GaAs wafer. The multilayer mirror 14 is in the state shown in the part (A) of FIG. 4. There will now be described a changeover operation from this state to the other state enabling the high-resolution X-ray analysis using AuLα1. In the part (B) of FIG. 10, the four-crystal monochromator 39 is inserted between the multilayer mirror 14 and the incident slit 38. Then, the multilayer mirror 14 is rotated counterclockwise by 0.057 degree as shown in the part (B) of FIG. 4. The rotation on of the multilayer mirror 14 slightly shifts the outgoing direction of the parallel beam 16, and therefore the goniometer base 40 is slightly moved upward in FIG. 10 so that the shifted parallel beam 16 can pass through the axis of rotation on 46 of the goniometer. With making such an adjustment, the parallel beam consisting of AuLα1 is taken out, and further the parallel beam is made monochromatic and is collimated by the four-crystal monochromator, and thereafter the high-resolution X-ray analysis is carried out using the parallel beam.

The high-resolution X-ray analysis is to mean a measurement that requires an angular resolution not more than 0.01 degree: for example, it corresponds to an X-ray diffraction measurement such as an X-ray diffraction measurement of a powder sample, a rocking curve measurement for estimation of the crystallinity of a thin film sample and a reciprocal space mapping measurement, and an X-ray reflectivity measurement.

Incidentally, the angular change of the multilayer mirror may be omitted. In a graph shown in FIG. 11, it is seen that even if the curve 36 (i.e., the multilayer mirror is adjusted so as to match the characteristic X-rays AuLα1) is used, the X-ray intensity at a wavelength around the K absorption edge of Ga keeps a certain degree. If such an X-ray intensity would not cause a problem in making the polarity judgment, the polarity judgment may be made under the condition on of the curve 36. In this case, the changeover operation shown in FIG. 10 is unnecessary, and therefore, in the state shown in the part (B) of FIG. 10, the four-crystal monochromator 39 is removed at first, and thereafter the polarity judgment is carried out, and then the four-crystal monochromator 39 is inserted to make the high-resolution X-ray analysis.

The present invention is not limited to the embodiment mentioned above, and the following modification may be made.

(1) Although, in the formulae (1) and (2) in FIG. 9, the intensity of diffracted X-ray beam at a wavelength longer than the absorption edge is an average of the intensities at two wavelengths and similarly the intensity of diffracted X-ray beam shorter than the absorption edge is also an average of the intensities at two wavelengths, there may be used the intensity of diffracted X-ray beam at only one wavelength, or alternatively it may be an average of intensities at three or more wavelengths.

(2) Although the above-described embodiment exemplifies GaAs as a sample having the polarity, the present invention is applicable to other single crystal samples. For example, a single crystal, which consists of a compound including Zn, Ga, Ge, As or Ta and has a polarity, may be examined for the polarity judgment using the Au target. In the case of a compound including Zn, the wavelength of the K absorption edge of Zn is 0.1283 nanometer. The multilayer mirror that has been adjusted so as to match around such a wavelength may be changed from the state shown in the part (A) of FIG. 4 to the other state (which allows AuL$\alpha$1 to be taken out) shown in the part (B) of FIG. 4 in a manner that the multilayer mirror is rotated clockwise by 0.005014 degree. Similarly, In the case of a compound including Ge, the wavelength of the K absorption on edge of Ge is 0.1117 nanometer. The multilayer mirror that has been adjusted so as to match around such a wavelength may be changed from the state shown in the part (A) of FIG. 4 to the other state (which allows AuL$\alpha$1 to be taken out) shown in the part (B) of FIG. 4 in a manner that the multilayer mirror is rotated counterclockwise by 0.11389 degree. Further, In the case of a compound including As, the wavelength of the K absorption edge of As is 0.1045 nanometer. The multilayer mirror that has been adjusted so as to match around such a wavelength may be changed from the state shown in the part (A) of FIG. 4 to the other state (which allows AuL$\alpha$1 to be taken out) shown in the part (B) of FIG. 4 in a manner that the multilayer mirror is rotated counterclockwise by 0.16546 degree. The positional relationships between the wavelengths of the K absorption on edge of Zn, Ge and As and AuL$\alpha$1 are seen in FIG. 11. Furthermore, In the case of a compound including Ta, the multilayer mirror is adjusted so as to use the wavelength of the L absorption edge ($L_1$=0.1059 nm, $L_2$=0.11124 nm and $L_3$=0.12542 nm) of Ta. A slight rotation on of the multilayer mirror can shift the multilayer mirror, which has been adjusted so as to match around such a wavelength, to the state allowing AuL$\alpha$1 to be taken out.

A compound that includes Zn and has the polarity may be ZnO and a certain solid solution crystal such as ZnO—MgO, ZnO—CoO and ZnO—CdO. A compound that includes Ga and has the polarity may be "III-V compound semiconductor crystal, which includes GaAs, GaP, GaSb, and solid solution crystal consisting of a combination on of one of such compounds and one of various crystals having a zinc-blende type structure such as InAs and AlP", "solid solution crystal having a so-called langasite-type structure such as $La_3Ga_5SiO_{14}$ and $La_3Ga_{5.5}Ta_{0.5}O_{14}$", "III-nitride compound semiconductor crystal, which includes GaN and crystal having a wurtzeit-type structure" and "solid solution crystal such as $LiGaO_2$ and $LiGaO_2$—$LiAlO_2$". A compound that includes Ge and has the polarity may be solid solution crystal having a so-called langasite-type structure such as $La_3Ga_5GeO_{14}$. A compound that includes As and has the polarity may be III-V compound semiconductor crystal, which includes GaAs, InAs, AlAs, and solid solution crystal consisting of a combination on of one of such compounds and one of various crystals having a zinc-blende type structure such as GaP and InPb. A compound that includes Ta and has the polarity may be solid solution crystal such as $LiTaO_3$—$LiNbO_3$ and $KTaO_3$—$KNbO_3$.

(3) Although the above-described embodiment uses the Au target as the X-ray source, a W (tungsten) target or Pt (platinum) target may be used occasionally to make the successful polarity judgment depending on a positional relationship between the wavelength of the absorption edge and the wavelength of the characteristic X-rays.

(4) The sample may be not only a single crystal but also an epitaxial thin film formed on a single crystal substrate.

(5) Although the above-described embodiment makes the X-ray intensity normalized with the use of the intensity of diffracted X-ray beam of the Si single crystal, such a normalization on may be omitted in the case of a small wavelength dependence of the intensity of incident X-ray beam.

(6) Although the embodiment shown in FIG. 1 exemplifies the rotating anode X-ray tube as the X-ray source, a sealed-off X-ray tube may be used.

The invention claimed is:

1. A method for judging a polarity of a single crystal sample, the method comprising the step of:
    (a) preparing a single crystal sample (18), which consists of plural elements and has a polarity;
    (b) preparing an X-ray source (10), which can generate X-rays in a predetermined wavelength range including an absorption edge of any one of the plural elements;
    (c) allowing a divergent X-ray beam (12) emitted from the X-ray source to be reflected by a parabolic multilayer mirror (14) to make a parallel beam that includes the X-rays in the predetermined wavelength range;
    (d) allowing the parallel beam, which is used as an incident X-ray beam, to be incident on the single crystal sample, and thereafter detecting an intensity of a diffracted X-ray beam (20) coming from the single crystal sample with an X-ray detector (22);
    (e) measuring a wavelength dependence of the intensity of diffracted X-ray beam in the wavelength range including the absorption edge of any one of the plural elements by synchronously scanning a rotation on angle $\omega$ of the single crystal sample to the incident X-ray beam and an angle $2\theta$ between the incident X-ray beam and the diffracted X-ray beam with an angular speed ratio of 1 to 2; and
    (f) acquiring a ratio of the intensity of diffracted X-ray beam shorter in wavelength than the absorption edge to the intensity of diffracted X-ray beam longer in wavelength than the absorption edge, and thereafter judging the polarity on a basis of a value of the ratio of intensity.

2. The polarity judging method according to claim 1, wherein the method further comprises the steps of:
    measuring the intensity of diffracted X-ray beam for also a reference sample having no polarity as in the case with the single crystal sample having the polarity;
    acquiring a normalized intensity of diffracted X-ray beam by dividing the intensity of diffracted X-ray beam at each wavelength in the single crystal sample by the intensity of diffracted X-ray beam at the same wavelength in the reference sample; and acquiring the ratio of intensity on a basis of the normalized intensity.

3. The polarity judging method according to claim 1, wherein the single crystal sample has a wafer shape.

4. The polarity judging method according to claim 1, wherein the single crystal sample is a single crystal film formed on a substrate.

5. The polarity judging method according to claim 1, wherein:
the single crystal sample is a compound including any one element selected from a group consisting of Ga, Zn, Ge and As;
the X-ray source has a target, whose material is any one selected from a group consisting of Au, W and Pt; and
the multilayer mirror is adjusted so as to reflect wavelengths around a K absorption edge of any one element selected from the group consisting of Ga, Zn, Ge and As.

6. The polarity judging method according to claim 1, wherein:
the single crystal sample is a compound including Ta;
the X-ray source has a target, whose material is any one selected from a group consisting of Au, W and Pt; and
the multilayer mirror is adjusted so as to reflect wavelengths around an L absorption edge of Ta.

7. An apparatus for judging a polarity of a single crystal sample, the apparatus comprising:
(a) an X-ray tube (10) having a target, which is made of a predetermined material;
(b) a parabolic multilayer mirror (14), which reflects X-rays (12) emitted from the X-ray tube to convert it to a parallel beam (16);
(c) a sample holder for holding a single crystal sample (18), which consists of plural elements and has a polarity;
(d) an X-ray detector (22) for detecting a diffracted X-ray beam (20) coming from the single crystal sample;
(e) a control device for synchronously scanning a rotation on angle ω of the single crystal sample to the parallel beam and an angle 2θ between the parallel beam and the X-ray detector;
(f) measurement instructing means for allowing the parallel beam, which is used as an incident X-ray beam, to be incident on the single crystal sample, and thereafter detecting an intensity of diffracted X-ray beam coming from the single crystal sample with an X-ray detector, and further measuring a wavelength dependence of the intensity of diffracted X-ray beam in a wavelength range including an absorption edge of any one of the plural elements by synchronously scanning the angle ω and the angle 2θ with an angular speed ratio of 1 to 2; and
(g) judging means for acquiring a ratio of the intensity of diffracted X-ray beam shorter in wavelength than the absorption edge to the intensity of diffracted X-ray beam longer in wavelength than the absorption edge, and thereafter judging the polarity on a basis of a value of the ratio of intensity.

8. The polarity judging apparatus according to claim 7, wherein the multilayer mirror is adjustable in angle to the X-rays emitted from the X-ray tube.

9. The polarity judging apparatus according to claim 7, wherein:
the material of the target is any one selected from a group consisting of Au, W and Pt; and
the multilayer mirror is adjustable so as to reflect wavelengths around a K absorption edge of any one element selected from the group consisting of Ga, Zn, Ge and As.

10. The polarity judging apparatus according to claim 7, wherein:
the material of the target is any one selected from a group consisting of Au, W and Pt; and
the multilayer mirror is adjustable so as to reflect wavelengths around an L absorption edge of Ta.

11. The polarity judging apparatus according to claim 7, wherein:
the material of the target is any one selected from a group consisting of Au, W and Pt; and
the multilayer mirror is adjustable so as to selectively reflect wavelengths around a K absorption edge of any one element selected from the group consisting of Ga, Zn, Ge and As, and a wavelength of characteristic X-rays of the target.

12. The polarity judging apparatus according to claim 7, wherein:
the material of the target is any one selected from a group consisting of Au, W and Pt; and
the multilayer mirror is adjustable so as to selectively reflect wavelengths around an L absorption edge of Ta, and a wavelength of characteristic X-rays of the target.

* * * * *